(12) United States Patent
Tamura et al.

(10) Patent No.: US 10,646,301 B2
(45) Date of Patent: May 12, 2020

(54) MEDICAL OBSERVATION APPARATUS AND MEDICAL OBSERVATION SYSTEM

(71) Applicant: Sony Olympus Medical Solutions Inc., Tokyo (JP)

(72) Inventors: Shigeru Tamura, Tokyo (JP); Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 42 days.

(21) Appl. No.: 15/751,993

(22) PCT Filed: Jul. 11, 2016

(86) PCT No.: PCT/JP2016/070468
§ 371 (c)(1),
(2) Date: Feb. 12, 2018

(87) PCT Pub. No.: WO2017/029907
PCT Pub. Date: Feb. 23, 2017

(65) Prior Publication Data
US 2018/0235721 A1    Aug. 23, 2018

(30) Foreign Application Priority Data

Aug. 20, 2015 (JP) ................................. 2015-163066

(51) Int. Cl.
*G02B 21/24* (2006.01)
*A61B 90/25* (2016.01)
(Continued)

(52) U.S. Cl.
CPC .............. *A61B 90/25* (2016.02); *A61B 90/35* (2016.02); *G02B 7/001* (2013.01);
(Continued)

(58) Field of Classification Search
CPC .... A61B 34/30; A61B 90/25; G02B 21/0012; G02B 21/24; G02B 21/00
(Continued)

(56) References Cited

U.S. PATENT DOCUMENTS

| 3,776,614 A * | 12/1973 | Kloots | ................... G02B 7/001 |
| | | | 359/376 |
| 4,548,373 A | 10/1985 | Komura | |
| 2006/0170384 A1 | 8/2006 | Kumagai et al. | |

FOREIGN PATENT DOCUMENTS

| JP | 60-135107 U | 9/1985 |
| JP | 5-29511 U | 4/1993 |

(Continued)

OTHER PUBLICATIONS

International Search Report dated Sep. 13, 2016, in PCT/JP2016/070468, filed Jul. 11, 2016.

*Primary Examiner* — Hung X Dang
(74) *Attorney, Agent, or Firm* — Xsensus LLP (57) ABSTRACT

A medical observation apparatus includes: a microscope; a support that movably supports the microscope, and includes plural arm portions and plural joint portions each of which connects two of the arm portions and rotatably holds one of the arm portions around a predetermined shaft portion with respect to the other of the arm portions; and one or plural cables inserted into an interior of the support. The shaft portion has a cylindrical shape into which the one or the plural cables can be inserted. A joint portion, of the plural joint portions, that connects two arm portions in which extending directions are orthogonal to each other includes a rotating portion rotatable according to rotational power of the shaft portion, and a restraining portion positioned where a central axis thereof is offset from a central axis and that is capable of restraining rotation of the rotating portion.

20 Claims, 7 Drawing Sheets

(51) Int. Cl.
  *A61B 90/35* (2016.01)
  *G02B 7/00* (2006.01)
  *G02B 21/00* (2006.01)
  *A61B 90/30* (2016.01)
  *A61B 90/50* (2016.01)

(52) U.S. Cl.
  CPC ......... *G02B 21/0012* (2013.01); *G02B 21/24* (2013.01); *A61B 90/30* (2016.02); *A61B 90/50* (2016.02); *A61B 2090/506* (2016.02); *A61B 2090/508* (2016.02)

(58) Field of Classification Search
  USPC .................................. 351/245; 359/384, 386
  See application file for complete search history.

(56) References Cited

FOREIGN PATENT DOCUMENTS

| | | |
|---|---|---|
| JP | 6-190774 A | 7/1994 |
| JP | 2001-242386 A | 9/2001 |
| JP | 2005-143970 A | 6/2005 |

\* cited by examiner

MEDICAL OBSERVATION APPARATUS AND MEDICAL OBSERVATION SYSTEM

TECHNICAL FIELD

The present invention relates to a medical observation apparatus and a medical observation system.

BACKGROUND ART

An optical microscope system has been conventionally known as a medical observation system to observe a microscopic part in the brain, heart, and the like of a patient that is an observation target at the time of performing medical surgery on the microscopic part. The optical microscope system includes an optical magnification system that magnifies the microscopic part (for example, see Patent Literature 1).

The microscope system disclosed in Patent Literature 1 includes a microscope unit in which an imaging unit is incorporated, and a support portion that includes a plurality of arms provided to be rotatable with respect to each other, and that supports the microscope unit. By rotating each of the arms, the microscope system can move or tilt the microscope unit three-dimensionally to a desired position.

Each of the arms is provided with an electromagnetic brake that prohibits its rotation. The electromagnetic brake is provided, for example, in an axial direction of a rotational shaft, and attracts an armature attached to the rotational shaft of the arm and fixes the armature to the electromagnetic brake, and thereby restrains the rotation of the rotational shaft via the armature. The electromagnetic brake releases the state of attracting the armature, for example, in a state where an operation switch is depressed, and allows the rotational shaft of each arm to rotate.

CITATION LIST

Patent Literature

Patent Literature 1: Japanese Laid-open Patent Publication No. 2001-242386

DISCLOSURE OF INVENTION

Technical Problem

In the microscope system, in order to downsize the support means, it is desired to insert a cable including a plurality of transmission lines for transmitting a signal for controlling the operation or the like of the imaging unit into the interior of the arm. When the cable is inserted into the interior of the arm, it is necessary to make a hole into which the cable is inserted in the rotational shaft and the electromagnetic brake. In this case, the electromagnetic brake becomes larger than necessary, which results in an obstacle to downsizing of the support means.

The present invention has been made in view of the above, and an object of the present invention is to provide a medical observation apparatus and a medical observation system capable of realizing the downsizing even if an electromagnetic brake is provided.

Solution to Problem

In order to solve the above problem and to achieve the object, a medical observation apparatus according to the present invention includes: a microscope unit that captures a magnified image of a microscopic part of an observation target and outputs an imaging signal thereof; a support unit that movably supports the microscope unit, and includes a plurality of arm portions and a plurality of joint portions each of which connects two of the arm portions and rotatably holds one of the two arm portions around a predetermined shaft portion with respect to the other one of the two arm portions; and one or a plurality of cables connected to the microscope unit and inserted into an interior of the support unit, wherein the shaft portion has a cylindrical shape into which the one or the plurality of cables can be inserted, and a joint portion, of the plurality of joint portions, that connects two arm portions in which an extending direction of one of the arm portions and an extending direction of the other one of the arm portions are orthogonal to each other, includes: a rotating portion that is rotatable according to rotational power of the shaft portion, and a restraining portion that is provided at a position where a central axis thereof is offset from a central axis of the shaft portion and that can restrain the rotation of the rotating portion.

In the medical observation apparatus according to the present invention, the restraining portion is an electromagnet that generates a magnetic field by energization, and the rotating portion has magnetism.

In the medical observation apparatus according to the present invention, the rotating portion is attached to an end portion in a direction of the central axis of the shaft portion.

In the medical observation apparatus according to the present invention, the joint portion that connects the two arm portions in which the extending direction of the one of the two arm portions and the extending direction of the other one of the two arm portions are orthogonal to each other, further includes: a first gear attached to an end portion in the direction of the central axis of the shaft portion and rotatable around the central axis of the shaft portion, and a second gear meshing with the first gear, and the rotating portion is rotatable in conjunction with the rotation of the second gear.

In the medical observation apparatus according to the present invention the joint portion that connects the two arm portions in which the extending direction of the one of the two arm portions and the extending direction of the other one of the two arm portions are orthogonal to each other, further includes: a first gear attached to an end portion in the direction of the central axis of the shaft portion and rotatable around the central axis of the shaft portion, a second gear provided apart from the first gear and rotatable around a predetermined axis, and a belt that is wound around the first and second gears and couples the two gears, and the rotating portion is rotatable in conjunction with the rotation of the second gear.

The medical observation apparatus according to the present invention, the electromagnet has a cylindrical shape, and a diameter of a hollow portion of the electromagnet is smaller than a diameter of a hollow portion of the shaft portion.

In the medical observation apparatus according to the present invention, the restraining portion is arranged outside an area which is an area extending from the shaft portion and extending in the direction of the central axis of the shaft portion according to an outer circumference of the shaft portion.

In the medical observation apparatus according to the present invention, the joint portion that connects the two arm portions in which the extending direction of the one of the two arm portions and the extending direction of the other one of the two arm portions are orthogonal to each other is a joint portion that connects a first arm portion holding the microscope unit and a second arm portion extending in a direction orthogonal to an extending direction of the first arm portion.

A medical observation system according to the present invention includes: a medical observation apparatus according to the present invention above; and a display device that displays an image corresponding to image data generated by the medical observation apparatus.

Advantageous Effects of Invention

According to the present invention, an effect is brought about, according to which downsizing can be realized even if an electromagnetic brake is provided.

BEST MODE FOR CARRYING OUT THE INVENTION

A mode for carrying out the present invention (hereinafter, "embodiment") will be described below with reference to the accompanying drawings. The present invention is not limited to the embodiment. Further, in the descriptions of the drawings, like parts are denoted by like reference signs. The diagrams are merely schematic, and may include a section where the dimensional relation or ratio between components differs between the drawings.

(First Embodiment)

Figure 1:
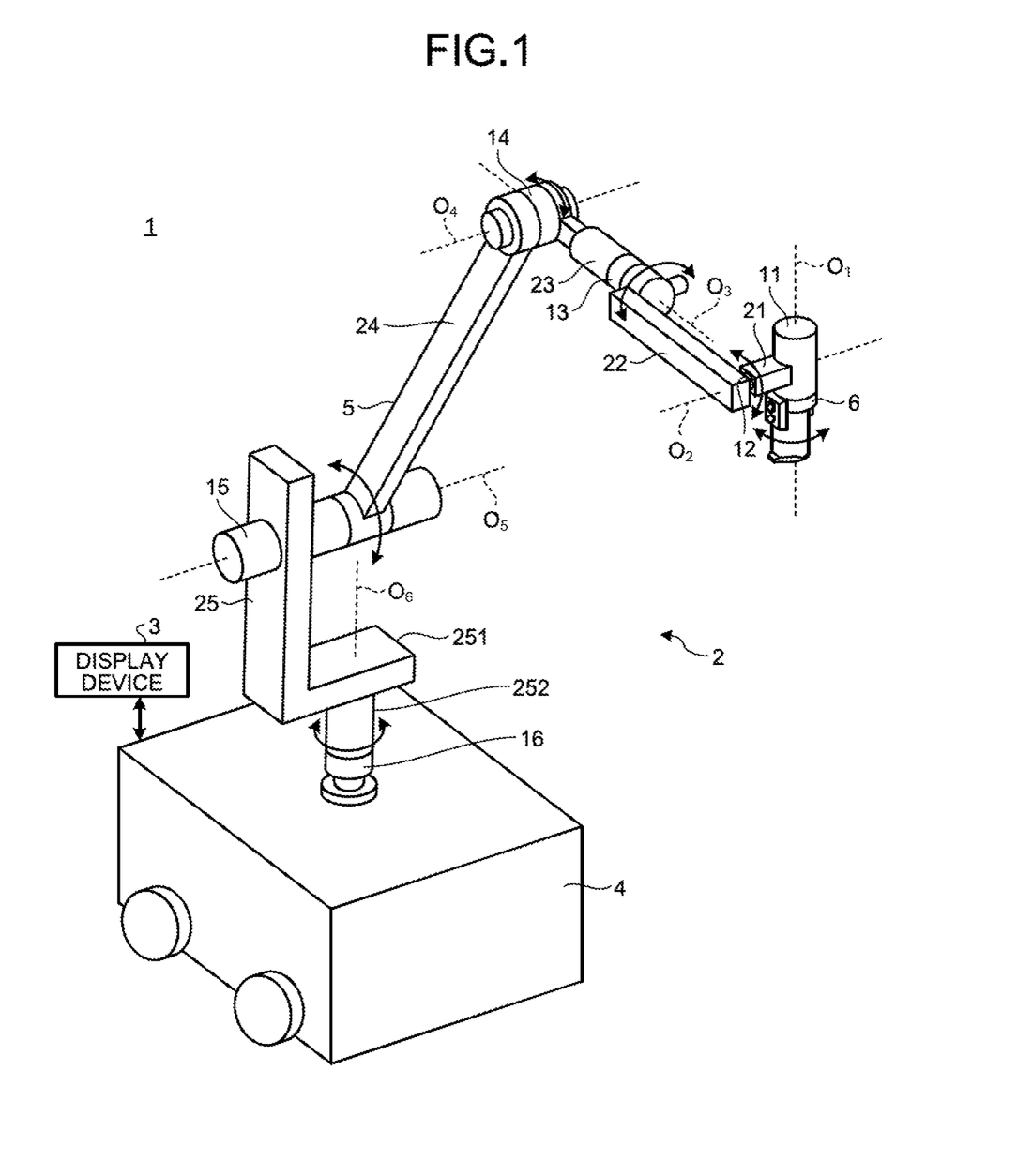
FIG. 1 is a perspective view illustrating an external appearance configuration of a medical observation system according to a first embodiment of the present invention.

FIG. 1 is a perspective view illustrating an external appearance configuration of a medical observation system according to an embodiment of the present invention. A medical observation system 1 illustrated in FIG. 1 includes a medical observation apparatus (hereinafter, "observation apparatus") 2 that functions as a microscope that magnifies and images a microscopic structure of an observation target, and a display device 3 that displays an image corresponding to image data generated by the observation apparatus 2.

The observation apparatus 2 includes a base unit 4 that constitutes a base of the observation apparatus 2 and is movable on the floor, a support unit 5 that is supported by the base unit 4, and a microscope unit 6 with a columnar shape that is provided at a distal end of the support unit 5 and that magnifies and images a microscopic part of the observation target. In the base unit 4, a control unit and a light source unit are provided. The control unit generates image data on the basis of a signal of an image captured by the microscope unit 6 and integrally controls the operation of the medical observation system 1. The light source unit emits illumination light to illuminate the observation target. In the observation apparatus 2, for example, a cable group is provided to stretch from the base unit 4 to the microscope unit 6. The cable group includes a transmission cable including a signal line through which a signal is transmitted between the control unit and the microscope unit 6, and a light guide cable through which illumination light is guided from the light source unit to the microscope unit 6. The cable group is provided along the support unit 5.

The support unit 5 includes a first joint portion 11, a first arm portion 21, a second joint portion 12, a second arm portion 22, a third joint portion 13, a third arm portion 23, a fourth joint portion 14, a fourth arm portion 24, a fifth joint portion 15, a fifth arm portion 25, and a sixth joint portion 16.

The support unit 5 includes four sets of two arm portions with a joint portion connecting one (on the distal-end side) of the two arm portions rotatably to the other (on the proximal-end side). Specifically, these four sets are (the first arm portion 21, the second joint portion 12, and the second arm portion 22), (the second arm portion 22, the third joint portion 13, and the third arm portion 23), (the third arm portion 23, the fourth joint portion 14, and the fourth arm portion 24), and (the fourth arm portion 24, the fifth joint portion 15, and the fifth arm portion 25).

The first joint portion 11 holds on its distal-end side the microscope unit 6 rotatably, while being held on its proximal-end side by the first arm portion 21 in a fixed state at a distal-end portion of the first arm portion 21. The first joint portion 11 has a cylindrical shape and holds the microscope unit 6 rotatably about a first axis $O_1$ that is the central axis of the first joint portion 11 in its height direction. The first arm portion 21 has a shape extending from a lateral surface of the first joint portion 11 in a direction perpendicular to the first axis $O_1$.

The second joint portion 12 holds on its distal-end side the first arm portion 21 rotatably, while being held on its proximal-end side by the second arm portion 22 in a fixed state at a distal-end portion of the second arm portion 22. The second joint portion 12 has a cylindrical shape and holds the first arm portion 21 rotatably about a second axis $O_2$ that is the central axis of the second joint portion 12 in its height direction and perpendicular to the first axis $O_1$. The second arm portion 22 has a substantial L-shape, and connects to the second joint portion 12 at one end portion of the L-shape (the end portion in a longitudinal line section). Details of the second joint portion 12 will be explained later.

The third joint portion 13 holds on its distal-end side the other end portion of the L-shape (the end portion in a transverse line section) of the second arm portion 22 rotatably. Simultaneously, the third joint portion 13 is held on its proximal-end side by the third arm portion 23 in a fixed state at a distal-end portion of the third arm portion 23. The third joint portion 13 has a cylindrical shape and holds the second arm portion 22 rotatably about a third axis $O_3$ that is the central axis of the third joint portion 13 in its height direction, perpendicular to the second axis $O_2$, and parallel to the direction in which the second arm portion 22 extends. The third arm portion 23 has a cylindrical shape on its distal-end side. On the proximal-end side thereof, a hole that passes therethrough is formed in a direction perpendicular to the height direction of the distal-end side cylinder. The third joint portion 13 is held rotatably by the fourth joint portion 14 through this hole.

The fourth joint portion 14 holds on its distal-end side the third arm portion 23 rotatably, while being held on its proximal-end side by the fourth arm portion 24 in a fixed state at the fourth arm portion 24. The fourth joint portion 14 has a cylindrical shape and holds the third arm portion 23 rotatably about a fourth axis $O_4$ that is the central axis of the fourth joint portion 14 in its height direction and perpendicular to the third axis $O_3$.

The fifth joint portion 15 holds on its distal-end side the fourth arm portion 24 rotatably, while being fixedly attached on its proximal-end side to the fifth arm portion 25. The fifth joint portion 15 has a cylindrical shape and holds the fourth arm portion 24 rotatably about a fifth axis $O_5$ that is the central axis of the fifth joint portion 15 in its height direction and parallel to the fourth axis $O_4$. The fifth arm portion 25 is constituted by a bent portion 251 that is bent to have an L-shape, and a bar-shaped portion 252 that extends downward from a bottom surface of the bent portion 251 in a bar shape. The fifth joint portion 15 is attached on its proximal-end side to an end portion of the bent portion 251, which is opposite to the portion from which the bar-shaped portion 252 extends.

The sixth joint portion 16 holds on its distal-end side the fifth arm portion 25 rotatably, while being fixedly attached on its proximal-end side to a top surface of the base unit 4. The sixth joint portion 16 has a cylindrical shape and holds the fifth arm portion 25 rotatably about a sixth axis $O_6$ that is the central axis of the sixth joint portion 16 in its height direction and perpendicular to the fifth axis $O_5$. The proximal-end portion of the bar-shaped portion 252 of the fifth arm portion 25 is attached on the distal-end side of the sixth joint portion 16.

The support unit 5 having the configuration as described above achieves motion of the micro-scope unit 6 with six different degrees of freedom in total, including three different degrees of freedom in translational motion, and three different degrees of freedom in rotational motion. The cables described above are inserted through the interior of the first joint portion 11 to the sixth joint portion 16 and the first arm portion 21 to the fifth arm portion 25, so as to connect the base unit 4 and the microscope unit 6.

Each of the first joint portion 11 to the sixth joint portion 16 includes an electromagnetic brake that individually prohibits the microscope unit 6 and the first arm portion 21 to the fifth arm portion 25 from rotating. Each electromagnetic brake is released in a state in which an operation switch, described later, provided in the microscope unit 6 is depressed, and then individually allows the microscope unit 6 and the first arm portion 21 to the fifth arm portion 25 to rotate.

The microscope unit 6 has a cylindrical shape, and is provided therein with an imaging unit that magnifies and captures an image of the observation target. The microscope unit 6 is further provided with an operation switch that receives an input operation to release the electromagnetic brakes in the first joint portion 11 to the sixth joint portion 16, and allow each of the joint portions to rotate, and an operation lever capable of changing magnification factors and the focal distance to the observation target in the imaging unit. The optical axis of the imaging unit corresponds with, for example, the first axis $O_2$.

The imaging unit images the observation target and outputs a signal of the image under control of the control unit. The imaging unit is configured by using an imaging element such as a Charge Coupled Device (CCD), a Complementary Metal Oxide Semiconductor (CMOS), or the like that receives an optical image of the observation target and converts the image to an electric signal.

Figure 2:
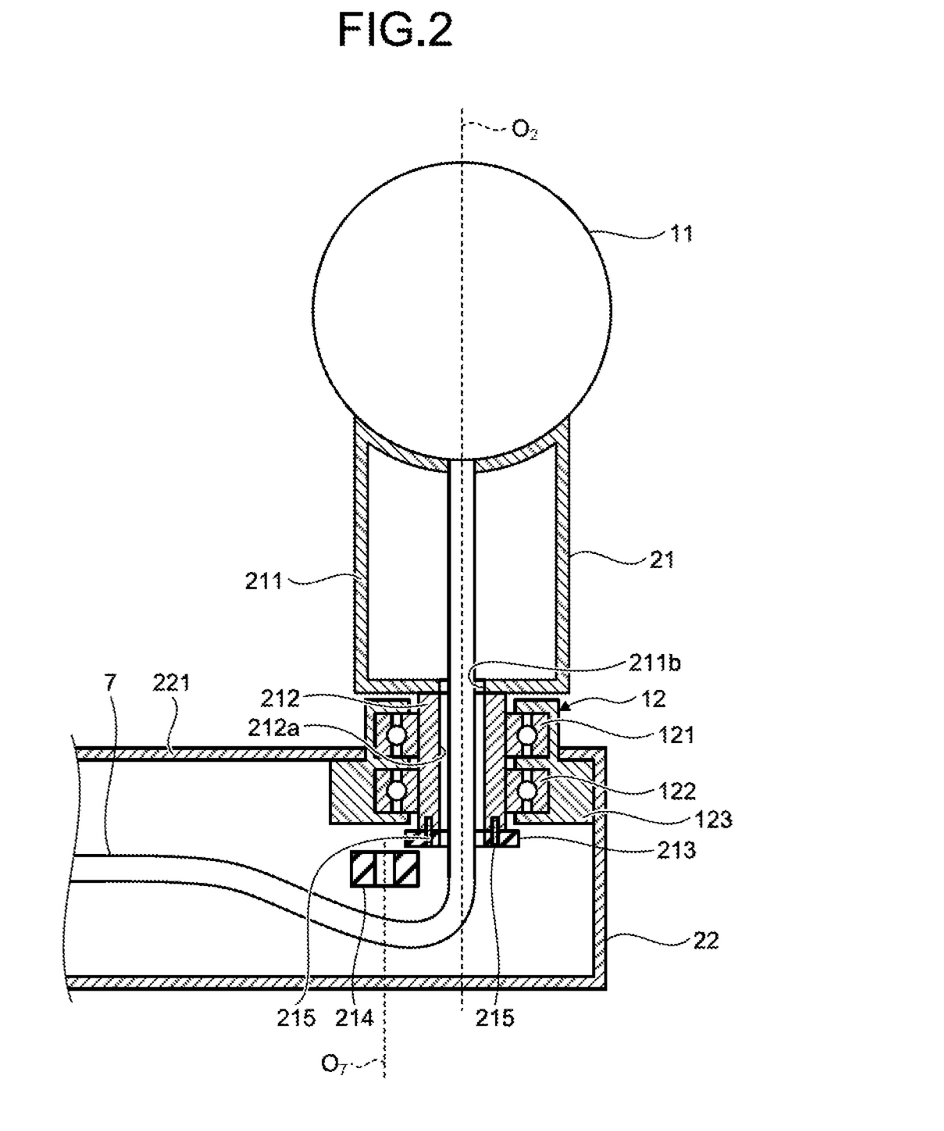
FIG. 2 is a partial cross-sectional view illustrating a configuration of relevant parts of the medical observation system according to the first embodiment of the present invention.

FIG. 2 is a partial cross-sectional view illustrating a configuration of a relevant part of the medical observation system according to the first embodiment, and is a partial cross-sectional view illustrating a configuration of a relevant part of the second joint portion 12, the first arm portion 21, and the second arm portion 22 when an electromagnet explained later is in a non-energized state. In the following description, it is assumed that a cable group 7 inserted through the support unit 5 includes, for example, the light guide cable and the transmission cable.

In the observation apparatus 2, the cable group 7 including a plurality of thin wire coaxial cables extending from the first joint portion 11 to the first arm portion 21 extends from the first arm portion 21 to the interior of the second arm portion 22 via the second joint portion 12. The first arm portion 21 includes an outer shell 211 fixedly attached to the first joint portion 11 and a hollow cylindrical shaft portion 212 in which a hollow portion 212a, extending along the second axis $O_2$ at the base end side of the outer shell 211 and communicated with a hollow portion 211b formed on the base end side of the outer shell 211, is formed.

The second joint portion 12 includes two shaft supporting portions 121 and 122 that rotatably support the shaft portion 212, and a holding portion 123 that is fixedly attached to an outer shell 221 of the second aria portion 22 and fixes and holds the outer periphery of the shaft supporting portions 121 and 122.

The second joint portion 12 includes an armature 213 (rotating portion) that is supported by a support portion 215 extending from the shaft portion 212 in the direction of the second axis $O_2$, and an electromagnet 214 (restraining portion) that is provided apart from the shaft portion 212 and generates a magnetic field by energization. The electromagnetic brake is constituted by the armature 213 and the electromagnet 214.

The armature 213 is formed by using a magnetic material, has a hollow disk shape, and is supported by the support portion 215 so as to freely reciprocate in the direction of the second axis $O_2$. The diameter of the hollow portion of the armature 213 is substantially equal to the diameter of the hollow portion 212a, and may be larger than the diameter of the outer circumference of the cable group 7.

The electromagnet 214 is fixed to the interior of the second arm portion 22 by unillustrated fixing means, for example, by a fixing member attached to the inner wall of the second arm portion 22. The electromagnet 214 has a cylindrical shape, and is arranged at a position in which a central axis $O_7$ of the electromagnet 214 is parallel and offset to the second axis $O_2$. In the electromagnet 214, a length in the radial direction is smaller than a diameter of the outer circumference of the shaft portion 212, and a length in the direction of the central axis $O_7$ is smaller than a length of the shaft portion 212 in the direction of the second axis $O_2$. The diameter of the hollow portion of the electromagnet 214 is smaller than the diameter of the hollow portion 212a. The diameter of the hollow portion is the length in the direction orthogonal to the second axis $O_2$ and the central axis $O_7$. It is preferable that the electromagnet 214 be disposed outside an area which is an area extending from the shaft portion 212 and extending in the direction of the central axis of the shaft portion 212 (herein, second axis $O_2$) according to the outer circumference of the shaft portion 212 in that the radius of the curvature of the cable group 7 can be increased when the cable group 7 is bent to be inserted into the shaft portion 212. In addition, "offset" indicates that the second axis $O_2$ and the central axis $O_7$ are arranged in different positions when viewed from the direction of the second axis $O_2$.

The cable group 7 passes through the hollow portion 212a of the first arm portion 21 and through the hollow portion of the armature 213 to extend to the interior of the second arm portion 22.

When the electromagnet 214 is in a non-energized state, the armature 213 is not attracted to the electromagnet 214, and thus rotates in conjunction with the rotation of the shaft portion 212. Therefore, when the electromagnet 214 is in the non-energized state, the first arm portion 21 can rotate around the second axis $O_2$ with respect to the second arm portion 22.

Figure 3:
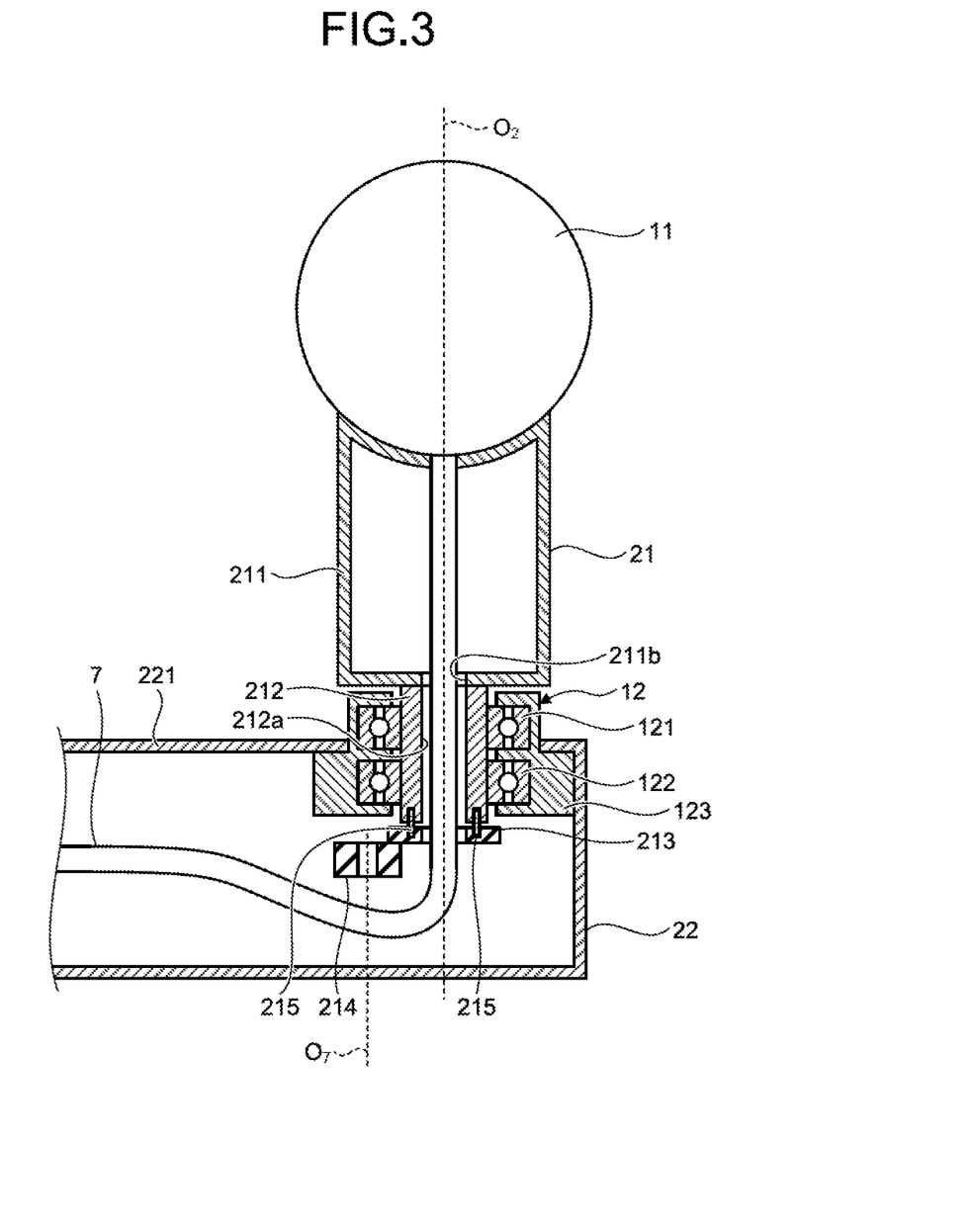
FIG. 3 is a partial cross-sectional view illustrating the configuration of the relevant parts of the medical observation system according to the first embodiment of the present invention.

FIG. 3 is a partial cross-sectional view illustrating the configuration of the relevant part of the medical observation system according to the first embodiment, and is a partial cross-sectional view illustrating the configuration of the relevant parts of the second joint portion 12, the first arm portion 21, and the second arm portion 22 when the electromagnet 214 is in an energized state. When the electromagnet 214 turns into an energized state and a magnetic field is generated from the electromagnet 214, the armature 213 is attracted to the electromagnet 214 and the rotation around the second axis $O_2$ of the armature 213 is restrained. Thereby the rotation of the shaft portion 212 that supports the armature 213 is also restrained.

Figure 4:
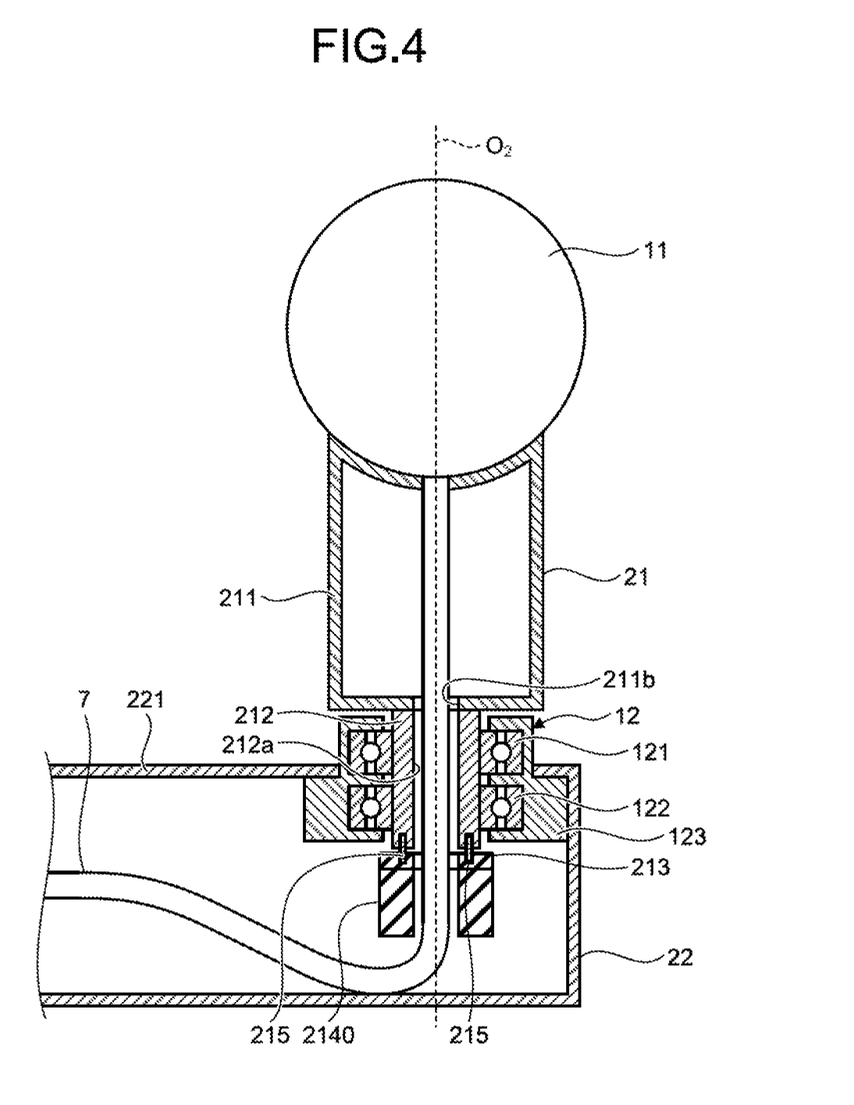
FIG. 4 is a partial cross-sectional view illustrating a configuration of relevant parts of a conventional medical observation system.

FIG. 4 is a partial cross-sectional view illustrating a configuration of a relevant part of a conventional medical observation system. When the central axis of an electromagnet 2140 and the central axis of the shaft portion 212 (second axis $O_2$) are aligned as in the conventional case, it is necessary to design the diameter of the hollow portion of the electromagnet 2140 to be substantially equal to the diameter of the hollow portion 212a in order to pass the cable group 7 through the hollow portion, which results in upsizing as compared with the electromagnet 214 illustrated in FIG. 2.

According to the first embodiment described above, in the electromagnetic brake that includes the armature 213, which is supported by the shaft portion 212, and the electromagnet 214 that restrains the rotation of the shaft portion 212 by attracting the armature 213 by the magnetic force, the central axis $O_7$ of the electromagnet 214 is arranged at a position which is parallel and offset to the second axis $O_2$, and the electromagnet 214 is arranged so as to be deviated with respect to the shaft portion 212 in the longitudinal direction of the second arm portion 22. Therefore, the electromagnet 214 can be arranged in the second arm portion 22 without being larger than necessary. With this, downsizing of the support unit 5 can be realized even if the electromagnetic brake is provided in the arm portion. When the support unit 5 is downsized, the area where the arm or the like blocks the field of view of an operator can be reduced, and therefore it is possible to enlarge the working area of the operator.

In the first embodiment described above, a member with magnetism, for example, an iron plate may be provided so as to extend from the end portion of the armature 213 in the direction orthogonal to the second axis $O_2$, so that the attraction to the electromagnet 214 is assisted by the member.

(Second Embodiment)

Figure 5:
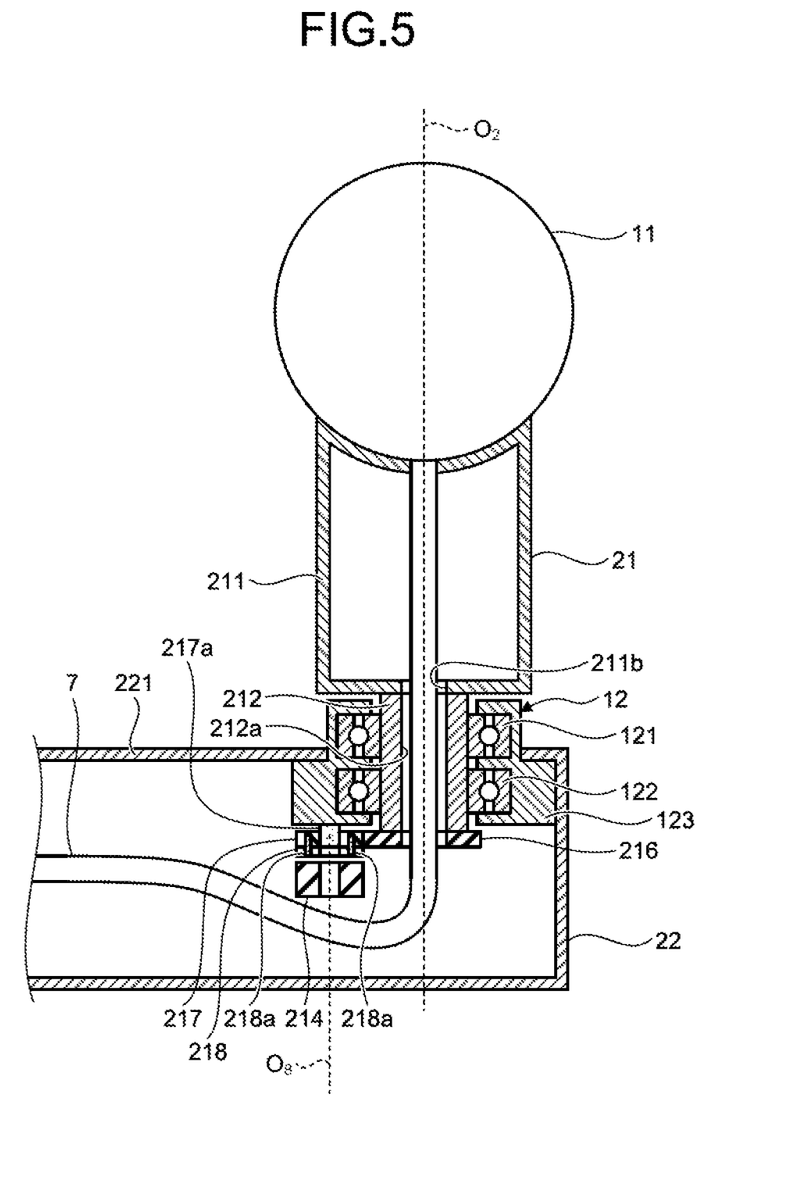
FIG. 5 is a partial cross-sectional view illustrating a configuration of relevant parts of a medical observation system according to a second embodiment of the present invention.

A second embodiment of the present invention will be explained next. FIG. 5 is a partial cross-sectional view illustrating a configuration of a relevant part of a medical observation system according to the second embodiment, and is a partial cross-sectional view illustrating a configuration of relevant parts of the second joint portion 12, the first arm portion 21, and the second arm portion 22 when the electromagnet 214 is in a non-energized state. The same reference signs are assigned to the same configuration as these described above, and an explanation will be provided. Although the first embodiment has explained that the armature 213 is directly attached to the shaft portion 212, the armature 213 is attached to the shaft portion 212 via a gear in the second embodiment.

In the second embodiment, the second joint portion 12 is provided with an electromagnetic brake including a first gear 216, a second gear 217, an armature 218 (rotating portion), and the electromagnet 214 (restraining portion).

The first gear 216 has a hollow disk shape rotatable around the second axis $O_2$ in conjunction with the rotation of the shaft portion 212. The diameter of the hollow portion of the first gear 216 is substantially equal to the diameter of the hollow portion 212a, and may be larger than the diameter of the outer circumference of the cable group 7.

The second gear 217 meshes with the first gear 216 and has a hollow disk shape rotatable around an axis $O_8$ by the rotation of the first gear 216, and is supported by the holding portion 123 via a support portion 217a.

The armature 218 is formed by using a magnetic material and has a hollow disk shape. The armature 218 is supported by a support portion 218a extending from the second gear 217 in the direction of the axis $O_8$ so as to freely reciprocate in the direction of the axis $O_8$. The axis $O_8$ is arranged in a position which is parallel and offset to the second axis $O_2$.

The electromagnet 214 is fixed to the inside of the second arm portion 22 by unillustrated fixing means, for example, by a fixing member attached to the inner wall of the second arm portion 22. The electromagnet 214 has a cylindrical shape, and the central axis of the electromagnet 214 coincides with the axis $O_8$. In other words, the central axis of the electromagnet 214 is arranged in a position which is parallel and offset to the second axis $O_2$. In the electromagnet 214, a length in the radial direction is smaller than a diameter of the outer circumference of the shaft portion 212 and a length in the direction of the central axis (axis $O_8$) is smaller than a length of the shaft portion 212 in the direction of the second axis $O_2$. The diameter of the hollow portion of the electromagnet 214 is smaller than the diameter of the hollow portion 212a.

In the second joint portion 12, when the shaft portion 212 rotates, the first gear 216 rotates around the second axis $O_2$ in conjunction with the rotation of the shaft portion 212. When the first gear 216 rotates around the second axis $O_2$, the second gear 217 meshed with the first gear 216 rotates around the axis $O_8$. At this time, the armature 218 rotates in conjunction with the rotation of the second gear 217.

When the electromagnet 214 is in a non-energized state, the armature 218 is not attracted to the electromagnet 214, and thus can rotate according to the rotation of the shaft portion 212. Therefore, when the electromagnet 214 is in the non-energized state, the first arm portion 21 can rotate around the second axis $O_2$ with respect to the second arm portion 22.

Figure 6:
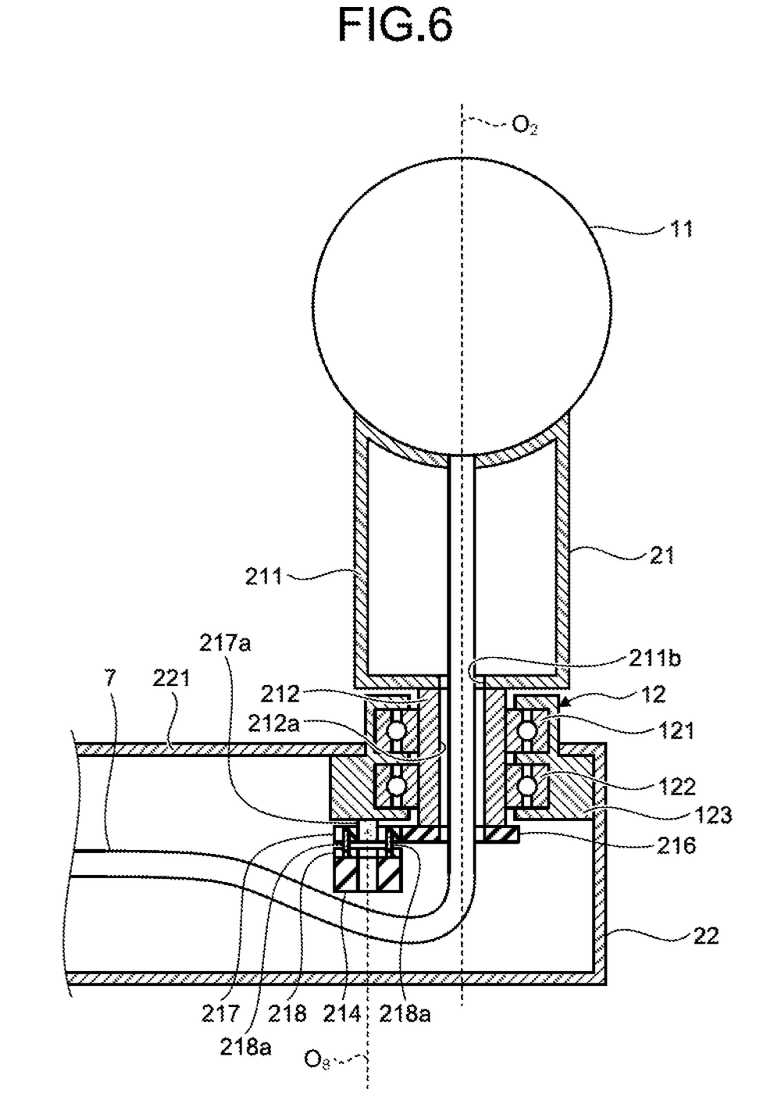
FIG. 6 is a partial cross-sectional view illustrating the configuration of the relevant parts of the medical observation system according to the second embodiment of the present invention.

FIG. 6 is a partial cross-sectional view illustrating the configuration of the relevant part of the medical observation system according to the second embodiment, and is a partial cross-sectional view illustrating the configuration of relevant parts of the second joint portion 12, the first arm portion 21, and the second arm portion 22 when the electromagnet 214 is in an energized state. When the electromagnet 214 turns into an energized state and a magnetic field is generated from the electromagnet 214, the armature 218 is attracted to the electromagnet 214 and the rotation of the armature 218 around the axis $O_8$ is restrained. At this time, the rotation of the second gear 217 that supports the armature 218 is also restrained. When the rotation of the second gear 217 is restrained, the rotation of the first gear 216 is also restrained, and, as a result, the rotation of the shaft portion 212 around the second axis $O_2$ is restrained According to the second embodiment described above, in the electromagnetic brake that includes the first gear 216 supported by the shaft portion 212, the second gear 217 supported by the holding portion 123 and meshed with the first gear 216, the armature 218 supported by the second gear 217, and the electromagnet 214 that restrains the rotation of the shaft portion 212 by attracting the armature 213 by the magnetic force, the central axis (axis $O_8$) of the electromagnet 214 is arranged at a position which is parallel and offset to the second axis $O_2$, and the electromagnet 214 is arranged so as to foe deviated with respect to the shaft portion 212 in the longitudinal direction of the second arm portion 22. Therefore, the electromagnet 214 can foe arranged in the second arm portion 22 without being larger than necessary. With this, downsizing of the support unit 5 can be realized even if the electromagnetic brake is provided in the arm portion. When the support unit 5 is downsized, the area where the arm or the like blocks the field of view of an operator can be reduced, and therefore it is possible to enlarge the working area of the operator.

(Modification of Second Embodiment)

Figure 7:
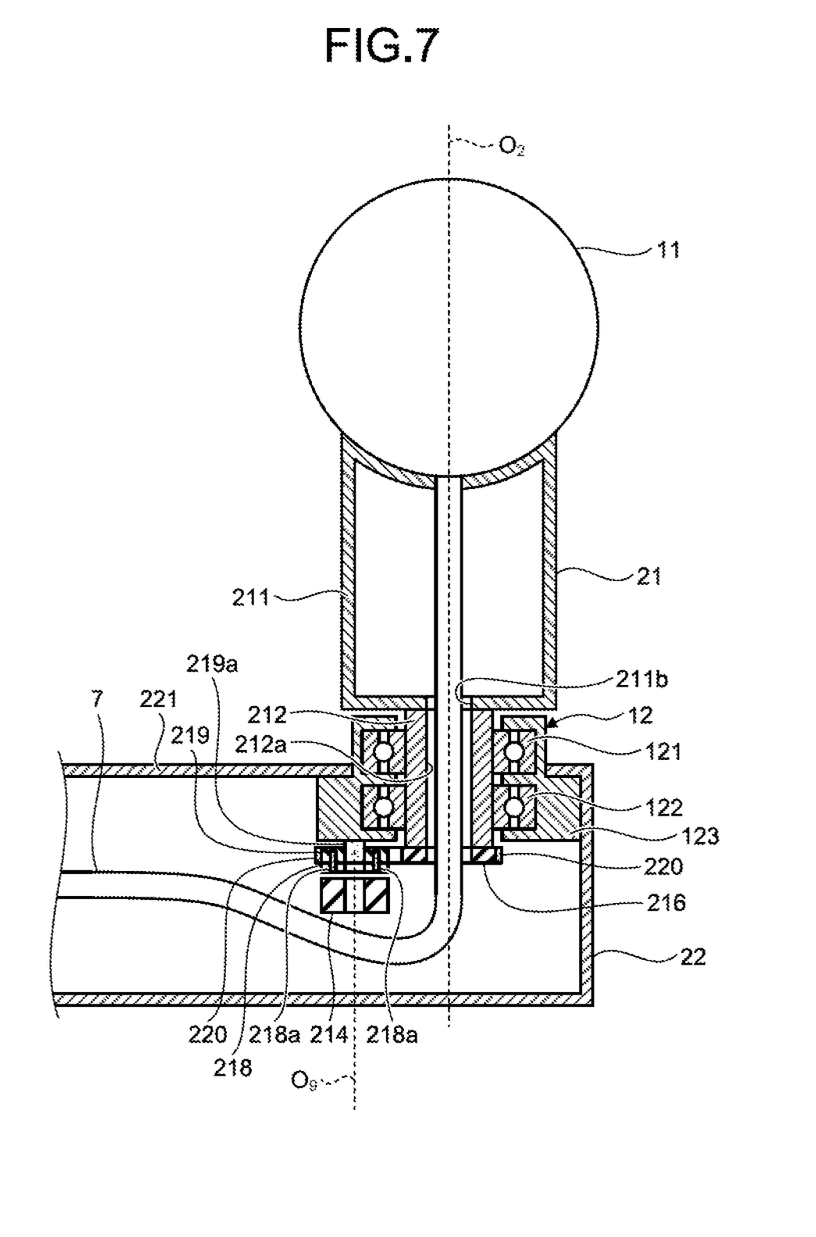
FIG. 7 is a partial cross-sectional view illustrating a configuration of relevant parts of a medical observation system according to a modification of the second embodiment of the present invention.

A modification of the second embodiment of the present invention will be explained below. FIG. 7 is a partial cross-sectional view illustrating a configuration of a relevant part of a medical observation system according to a modification of the second embodiment of the present invention, and is a partial cross-sectional view illustrating a configuration of relevant parts of the second joint portion 12, the first arm portion 21, and the second arm portion 22 when the electromagnet 214 is in a non-energized state. Although the second embodiment has explained that the two gears (the first gear 216 and the second gear 217) are meshed with each other and the rotational power of the shaft portion 212 is transmitted from the first gear 216 to the second gear 217, two gears (the first gear 216 and the second gear 217) are coupled by a belt, and the rotational power of the shaft portion 212 is transmitted from the first gear 216 to a second gear 219 via the belt.

In the present modification, the second joint portion 12 is provided with an electromagnetic brake including the second gear 219, a belt 220, the armature 218 (rotating portion), the first gear 216, and the electromagnet 214 (restraining portion).

The second gear 219 is provided apart from the first gear 216 and is supported by the holding portion 123 via a support portion 219a rotatable around an axis $O_9$. Therefore, the second gear 219 can rotate around the axis $O_9$. The armature 218 is supported by the support portion 218a extending from the second gear 219 in the direction of the axis $O_9$ so as to freely reciprocate in the direction of the axis $O_9$. The axis $O_9$ is arranged in a position which is parallel and offset to the second axis $O_2$.

The first gear 216 and the second gear 219 are coupled with the belt 220 that can be meshed with both of the gears.

In other words, when the first gear 216 rotates around the second axis $O_2$, the rotational power is transmitted to the second gear 219 via the belt 220, and the second gear 219 rotates around the axis $O_9$. Conversely, when the second gear 219 rotates around the axis $O_9$, the rotational power is transmitted to the first gear 216 via the belt 220, and the first gear 216 rotates around the second axis $O_2$.

The electromagnet 214 is fixed to the inside of the second arm portion 22 by unillustrated fixing means, for example, by a fixing member attached to the inner wall of the second arm portion 22. The electromagnet 214 has a cylindrical shape, and the central axis of the electromagnet 214 coincides with the axis $O_9$. In other words, the central axis of the electromagnet 214 is arranged at a position which is parallel and offset to the second axis $O_2$. In the electromagnet 214, a length in the radial direction is smaller than a diameter of the outer circumference of the shaft portion 212 and a length in the direction of the central axis (axis $O_9$) is smaller than a length of the shaft portion 212 in the direction of the second axis $O_2$.

In the second joint portion 12, when the shaft portion 212 rotates, the first gear 216 rotates around the second axis $O_2$ in conjunction with the rotation of the shaft portion 212. When the first gear 216 rotates around the second axis $O_2$, the rotational power is transmitted to the second gear 219 via the belt 220, and the second gear 219 rotates around the axis $O_9$. At this time, the armature 218 rotates in conjunction with the rotation of the second gear 219.

When the electromagnet 214 is in a non-energized state, the armature 218 is not attracted to the electromagnet 214, and thus can rotate according to the rotation of the shaft portion 212. Therefore, when the electromagnet 214 is in the non-energized state, the first arm portion 21 can rotate around the second axis $O_2$ with respect to the second arm portion 22.

On the other hand, when the electromagnet 214 is in an energized state, the armature 218 is attracted to the electromagnet 214, and the rotation of the armature 218 around the axis $O_9$ is restrained. At this time, the rotation of the second gear 219 that supports the armature 218 is also restrained. When the rotation of the second gear 219 is restrained, the circulating movement of the belt 220 is restrained and the rotation of the first gear 216 is also restrained, and as a result, the rotation of the shaft portion 212 around the second axis $O_2$ is restrained.

According to the present modification, the advantageous effects according to the second embodiment can be obtained, the distance between the first gear 216 and the second gear 219 can be adjusted by the belt 220 that is wound around the first gear 216 and the second gear 219 thereby to couple the gears, and the flexibility in an arrangement of the electromagnet 214 can foe improved. In particular, because the second arm portion 22 has a spatial room in the longitudinal direction, the electromagnet 214 can be displaced along the longitudinal direction by adjusting the belt 220.

While the embodiments of the present invention have been described above, the present invention is not limited only to the above embodiments. In the first and the second embodiments, the configuration of the electromagnetic brake in the second joint portion 12 has been described as an example. However, such configuration is applicable to any joint portion, specifically, to a joint portion, of a plurality of joint portions, which connects two arm portions in which an extending direction of one arm portion and an extending direction of the other arm portion are orthogonal to each other.

In the first and the second embodiments, while the electromagnetic brake including at least the electromagnet and the armature has been explained as an example, an air brake may be applied instead of the electromagnetic brake. In the case of the air brake, it is possible to restrain the rotation of the shaft portion 212 by sucking and attracting a member corresponding to the armature by air.

In the above-described first and second embodiments, the observation apparatus 2 is described as including the cable group including a transmission cable through which a signal is transmitted, and a light guide cable through which illumination light is guided. In a case where the observation apparatus 2 does not include a light guide cable because of using an external light source device or the like, the observation apparatus 2 may include a single cable, e.g., one having only a transmission cable, or the like.

In the first and the second embodiments, when the microscope unit 6 has a plurality of imaging devices, the number of transmission cables in the cable group increases according to the number of imaging devices. As the number of transmission cables increases, the diameter of the outer circumference of the cable group 7 also increases. In the conventional configuration, it is necessary to increase the diameter of the hollow portion of the electromagnet according to the increase in the diameter of the cable group. However, in the configuration of the present invention, the same electromagnet can be used regardless of the increase in the diameter of the cable group.

INDUSTRIAL APPLICABILITY

As explained above, the medical observation apparatus and the medical observation system according to the present invention are useful in realizing the downsizing even if the electromagnetic brake is provided.

REFERENCE SIGNS LIST 1 medical observation system
2 medical observation apparatus
3 display device
4 base unit
5 support unit
6 microscope unit
11 first joint portion
12 second joint portion
13 third joint portion
14 fourth joint portion
15 fifth joint portion
16 sixth joint portion
21 first arm portion
22 second arm portion
23 third arm portion
24 fourth arm portion
25 fifth arm portion
121, 122 shaft supporting portion
123 holding portion
211 outer shell
212 shaft portion
213 218 armature
214 electromagnet
215, 217a, 219a support portion
216 first gear
217, 219 second gear
220 belt

The invention claimed is:

1. A medical observation apparatus comprising:
a microscope unit that captures a magnified image of a microscopic part of an observation target and outputs an imaging signal thereof;
a support unit that movably supports the microscope unit, and includes a plurality of arm portions and a plurality of joint portions each of which connects two of the arm portions and rotatably holds one of the two arm portions around a predetermined shaft portion with respect to the other one of the two arm portions; and
one or a plurality of cables connected to the microscope unit and inserted into an interior of the support unit, wherein
the shaft portion has a cylindrical shape into which the one or the plurality of cables can be inserted, and
the joint portion, of the plurality of joint portions, that connects two arm portions in which an extending direction of one of the arm portions and an extending direction of the other one of the arm portions are orthogonal to each other, includes:
a rotating portion that is rotatable according to rotational power of the shaft portion, and
a restraining portion that is provided at a position where a central axis thereof is offset from a central axis of the shaft portion and that can restrain the rotation of the rotating portion.

2. The medical observation apparatus according to claim 1, wherein
the restraining portion is an electromagnet that generates a magnetic field by energization, and
the rotating portion has magnetism.

3. The medical observation apparatus according to claim 2, wherein
the rotating portion is attached to an end portion in a direction of the central axis of the shaft portion.

4. The medical observation apparatus according to claim 2, wherein
the joint portion that connects the two arm portions in which the extending direction of the one of the two arm portions and the extending direction of the other one of the two arm portions are orthogonal to each other, further includes:
a first gear attached to an end portion in the direction of the central axis of the shaft portion and rotatable around the central axis of the shaft portion, and
a second gear meshing with the first gear, and
the rotating portion is rotatable in conjunction with the rotation of the second gear.

5. The medical observation apparatus according to claim 2, wherein
the joint portion that connects the two arm portions in which the extending direction of the one of the two arm portions and the extending direction of the other one of the two arm portions are orthogonal to each other, further includes:
a first gear attached to an end portion in the direction of the central axis of the shaft portion and rotatable around the central axis of the shaft portion,
a second gear provided apart from the first gear and rotatable around a predetermined axis, and
a belt that is wound around the first and second gears and couples the two gears, and
the rotating portion is rotatable in conjunction with the rotation of the second gear.

6. The medical observation apparatus according to claim 2, wherein
the electromagnet has a cylindrical shape, and
a diameter of a hollow portion of the electromagnet is smaller than a diameter of a hollow portion of the shaft portion.

7. The medical observation apparatus according to claim 1, wherein
the restraining portion is arranged outside an area which is an area extending from the shaft portion and extending in the direction of the central axis of the shaft portion according to an outer circumference of the shaft portion.

8. The medical observation apparatus according to claim 1, wherein
the joint portion that connects the two arm portions in which the extending direction of the one of the two arm portions and the extending direction of the other one of the two arm portions are orthogonal to each other is a joint portion that connects a first arm portion holding the microscope unit and a second arm portion extending in a direction orthogonal to an extending direction of the first arm portion.

9. A medical observation system comprising:
a medical observation apparatus according to claim 1; and
a display device that displays an image corresponding to image data generated by the medical observation apparatus.

10. A medical observation apparatus comprising:
an imaging device that captures an image of an observation target and outputs an imaging signal thereof;
a support that movably supports the imaging device, and includes a plurality of arms and a plurality joints each of which connects two of the arms rotatably around a shaft; and
one or a plurality of cables connected to the imaging device and inserted into an interior of the support, wherein
the shaft has a cylindrical shape into which the one or the plurality of cables are insertable therein, and
a joint of the plurality of joints includes:
an armature rotatable with the shaft, and
an electromagnet provided at a position where a central axis thereof is offset from a central axis of the shaft and is configured to restrain the rotation of the armature.

11. The medical observation apparatus of claim 10, wherein the imaging device comprises a microscope.

12. The medical observation apparatus of claim 10, wherein two arms of the plurality of arms connect at the joint and extend in different directions.

13. The medical observation apparatus of claim 12, wherein the different directions being orthogonal directions.

14. The medical observation apparatus according to claim 10, wherein the electromagnet is configured to generate a magnetic field by energization, and the armature exhibits magnetism.

15. The medical observation apparatus according to claim 14, wherein the armature is attached to an end portion in a direction of the central axis of the shaft.

16. The medical observation apparatus according to claim 14, wherein the joint includes:
a first gear attached to an end in the direction of the central axis of the shaft and rotatable around the central axis of the shaft, and
a second gear meshing with the first gear, and the armature is rotatable in conjunction with the rotation of the second gear.

17. The medical observation apparatus according to claim 14, wherein the joint includes:
a first gear attached to an end in the direction of the central axis of the shaft and rotatable around the central axis of the shaft,
a second gear provided apart from the first gear and rotatable around a predetermined axis, and
a belt that is wound around the first and second gears and couples the two gears, and the armature is rotatable in conjunction with the rotation of the second gear.

18. The medical observation apparatus according to claim 14, wherein the electromagnet has a cylindrical shape, and
a diameter of a hollow portion of the electromagnet is smaller than a diameter of a hollow portion of the shaft.

19. The medical observation apparatus according to claim 10, wherein the electromagnet is arranged outside an area which is an area extending from the shaft and extending in the direction of the central axis of the shaft according to an outer circumference of the shaft.

20. A medical observation system comprising:
a medical observation apparatus according to claim and
a display device that displays an image corresponding to image data generated by the medical observation apparatus.

* * * * *